(12) United States Patent
Mundwiler et al.

(10) Patent No.: US 8,303,307 B2
(45) Date of Patent: *Nov. 6, 2012

(54) HOLDING ELEMENT FOR A DENTAL IMPLANT

(75) Inventors: Ulrich Mundwiler, Tenniken (CH); Daniel Günter, Waldenburg (CH); Miodrag Lazic, Oberdorf BL (CH); Marcello Memmolo, Sissach (CH); Stéphane Courvoisier, Colombier (CH)

(73) Assignee: Straumann Holding AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/281,811

(22) Filed: Oct. 26, 2011

(65) Prior Publication Data

US 2012/0052462 A1    Mar. 1, 2012

Related U.S. Application Data

(63) Continuation of application No. 11/497,712, filed on Aug. 2, 2006, now Pat. No. 8,070,491.

(51) Int. Cl.
*A61C 3/00* (2006.01)
(52) U.S. Cl. ........................................ 433/163; 206/63.5
(58) Field of Classification Search .................. 433/141, 433/163, 173–174; 206/63.5
See application file for complete search history.

(56) References Cited

U.S. PATENT DOCUMENTS

| | | | |
|---|---|---|---|
| 4,856,648 A | 8/1989 | Krueger | |
| 5,328,371 A | 7/1994 | Hund et al. | |
| 5,368,160 A | 11/1994 | Leuschen et al. | |
| 5,538,428 A | 7/1996 | Staubli | |
| 5,558,230 A | 9/1996 | Fischer et al. | |
| 5,582,299 A | 12/1996 | Lazzara et al. | |
| 5,622,500 A | 4/1997 | Niznick | |
| 5,782,918 A | 7/1998 | Klardie et al. | |
| 5,996,779 A | 12/1999 | Klardie et al. | |
| 6,086,371 A | 7/2000 | Bassett et al. | |
| 6,099,311 A | 8/2000 | Wagner et al. | |
| 6,142,296 A | 11/2000 | Klardie et al. | |
| 6,217,332 B1 | 4/2001 | Kumar | |
| 6,247,931 B1 | 6/2001 | Sutter | |
| 6,261,097 B1 | 7/2001 | Schmutz et al. | |
| 6,280,192 B1 | 8/2001 | Groll et al. | |
| 6,312,260 B1 | 11/2001 | Kumar et al. | |
| 6,315,562 B1 | 11/2001 | Kumar | |
| 6,332,777 B1 | 12/2001 | Sutter | |
| 6,358,050 B1 | 3/2002 | Bergström et al. | |
| 6,394,806 B1 | 5/2002 | Kumar | |
| 6,394,809 B2 | 5/2002 | Rogers et al. | |
| 6,416,324 B1 | 7/2002 | Day | |
| 6,428,318 B2 | 8/2002 | Artal | |

(Continued)

FOREIGN PATENT DOCUMENTS

WO    WO 98/53755    12/1998

(Continued)

*Primary Examiner* — Cris L Rodriguez
*Assistant Examiner* — Hao D Mai
(74) *Attorney, Agent, or Firm* — Scully, Scott, Murphy & Presser, P.C.

(57) ABSTRACT

Holding element for a dental implant including: an engagement section adapted for engagement with a manipulating tool; a retention section joined to the engagement section and adapted for engagement with a package, in particular an ampule; and a clamping section joined to the retention section and adapted for connecting the holding element to the dental implant, the clamping section including a force transmission element, wherein the clamping section further includes a clamping element provided with an elastic means extending in a non-compressed position thereof at and beyond the outer perimeter defined by the force transmission element.

12 Claims, 7 Drawing Sheets

U.S. PATENT DOCUMENTS

| | | |
|---|---|---|
| 6,517,543 B1 | 2/2003 | Berrevoets et al. |
| 6,561,805 B2 | 5/2003 | Kumar |
| 6,663,389 B1 | 12/2003 | Gallicchio |
| 6,827,575 B1 | 12/2004 | Jörneus |
| 6,913,465 B2 | 7/2005 | Howlett et al. |
| 6,955,258 B2 | 10/2005 | Howlett et al. |
| 7,207,801 B2 | 4/2007 | Vogt et al. |
| 7,300,284 B2 | 11/2007 | Linder |
| 7,484,959 B2 | 2/2009 | Porter et al. |
| 7,694,812 B2 | 4/2010 | Bammerlin et al. |
| 7,854,316 B2 | 12/2010 | Park et al. |
| 2001/0019816 A1 | 9/2001 | Kumar |
| 2003/0221977 A1 | 12/2003 | Kumar et al. |
| 2003/0224325 A1 | 12/2003 | Kumar et al. |
| 2004/0101808 A1 | 5/2004 | Porter et al. |
| 2004/0180308 A1 | 9/2004 | Ebi et al. |
| 2007/0072148 A1 | 3/2007 | Memmolo et al. |

FOREIGN PATENT DOCUMENTS

| | | |
|---|---|---|
| WO | WO 00/02496 | 1/2000 |
| WO | WO 01/50978 | 7/2001 |
| WO | WO 2005037126 A1 | 4/2005 |

HOLDING ELEMENT FOR A DENTAL IMPLANT

CROSS REFERENCE TO RELATED APPLICATIONS

The present application is a continuation of co-pending U.S. application Ser. No. 11/497,712, filed Aug. 2, 2006, the disclosure of which is hereby incorporated by reference.

The present invention relates in general to an improved holding element for a dental implant and in particular to an improved coupling of the holding element to the dental implant.

BACKGROUND OF THE INVENTION

As known for instance from U.S. Pat. No. 6,261,097, which has been assigned to the present assignee, dental implants may be stored prior to their use in a sealed ampule which is preferably filled with a storage fluid.

During storage the dental implant is temporarily coupled to a holding element which holding element is used in the course of storage to retain the dental implant firmly in position within the ampule. Later, when the dental implant is removed from the ampule for implantation into a respective bone, the holding element is gripped by the user to be placed into the implant site. The holding element is furthermore adapted for temporary positive attachment to manipulating tools that facilitate the removal of the dental implant from the ampule and the placement thereof into the bone at the implant site. Ultimately, when the dental implant is implanted at the desired site in the bone, the holding element may be removed from the dental implant. Nevertheless, as the holding element is screwed to the dental implant, the overall handling is tedious.

From WO-A1-2005/037126, which has also been assigned to the present assignee and the content of which is herewith incorporated by reference, there is known a holding element wherein the use of a screw for the coupling thereof to the dental implant is avoided.

As shown in FIGS. 1 through 3, that illustrate the prior art known from WO-A1-2005/037126, the known holding element which is generally designated by reference numeral 1 includes an engagement section 2 adapted for positive engagement with a manipulating tool not shown. The engagement section 2 is embodied as a polygonally shaped end, for instance as an octagonally shaped end. Adjacent to the engagement section 2 there is provided a radial groove 3 for accommodating an O-ring 3A shown in FIG. 2 that has a securing function to the manipulating tool not shown.

Furthermore, as indicated with particular reference to FIGS. 1 and 1A, the holding element 1 has a retention section 4 with two adjoining annular shoulders 5 and 7 and an intermediate cylindrical section 6 of a reduced diameter adapted for retention in an inner ampule indicated at 20. The retention section 4 is joined to the engagement section 2 by a breaking point member 30.

The known holding element 1 further includes, adjacent to the retention section 4, a clamping section 8 with a first radial groove 9, a force transmission element 10 with an octagonal shape for the positive engagement with a dental implant 14, a second radial groove 11 and a tapered member 12. As shown in FIG. 3, the second radial groove 11 is provided with a clamping or lock ring 13 made of PEEK (poly ether ether ketone) including a peripheral clearance 13A for facilitating the mounting thereof.

The dental implant 14, in turn, is provided with a cavity 15 having an inner surface 17 that matches the surface of the force transmission element 10, such as to provide for a positive engagement between the dental implant 14 and the holding element 1, whereby the dental implant 14 is rotationally secured to the holding element 1. The cavity 15 of the dental implant 14 further includes an undercut 18 sized for clampingly receiving the lock ring 13 and a conical terminal section 19 closely enclosing the first radial grove 9 of the clamping section 8 of the holding element 1.

While providing for a better handling and facilitating the separation of the dental implant from the holding element it has been nevertheless noted in the practical implementation that the known solution of WO-A1-2005/037126 still suffers some drawbacks, inasmuch the clamping force of the prior art PEEK lock ring 13 changes in time or is variable ad initio, and therefore it is difficult to precisely adjust the clamping force when the implantation is carried out. This problem is of particular concern if the dental implant is stored over a longer time span and is even further aggravated if the storage medium is a fluid.

In addition, the prior art lock ring tends to release carbon that may in turn damage the surface of a dental implant, particularly an SLA treated dental implant surface.

Furthermore, the manufacturing tolerances of the prior PEEK lock ring are very strict, and therefore the production thereof may become cumbersome.

SUMMARY OF THE INVENTION

The aim of the present invention is to provide for an improved holding element for a dental implant wherein the clamping force can be maintained over a larger time span during which the holding element and the dental implant are stored in an packaging. The above aim applies to packaging with or without storage fluids.

Within the scope of this aim, an object of the present invention is to provide a holding element for a dental implant wherein the clamping force can be precisely adjusted.

Another object of the present invention is to provide for a holding element that minimizes the likelihood of damaging the dental implant and that does not require excessively strict manufacturing tolerances.

This aim, and these and other objects which will become better apparent hereinafter, are achieved by a holding element for a dental implant as defined in the appended claims.

BRIEF DESCRIPTION OF THE DRAWINGS

Further characteristics and advantages of the present invention will become better apparent from the following description of some preferred but not exclusive embodiments of a holding element for a dental implant according to the invention, illustrated by way of non-limitative examples in the accompanying drawings, wherein.

DESCRIPTION OF THE PREFERRED EMBODIMENTS

Figure 3:
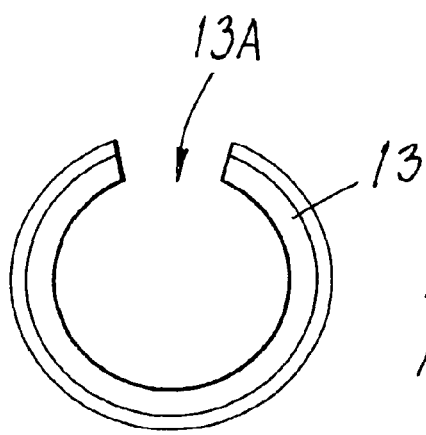
FIG. 3 shows a top view of a PEEK clamping or lock ring of the prior art holding element of FIG. 1.
Figure 4:
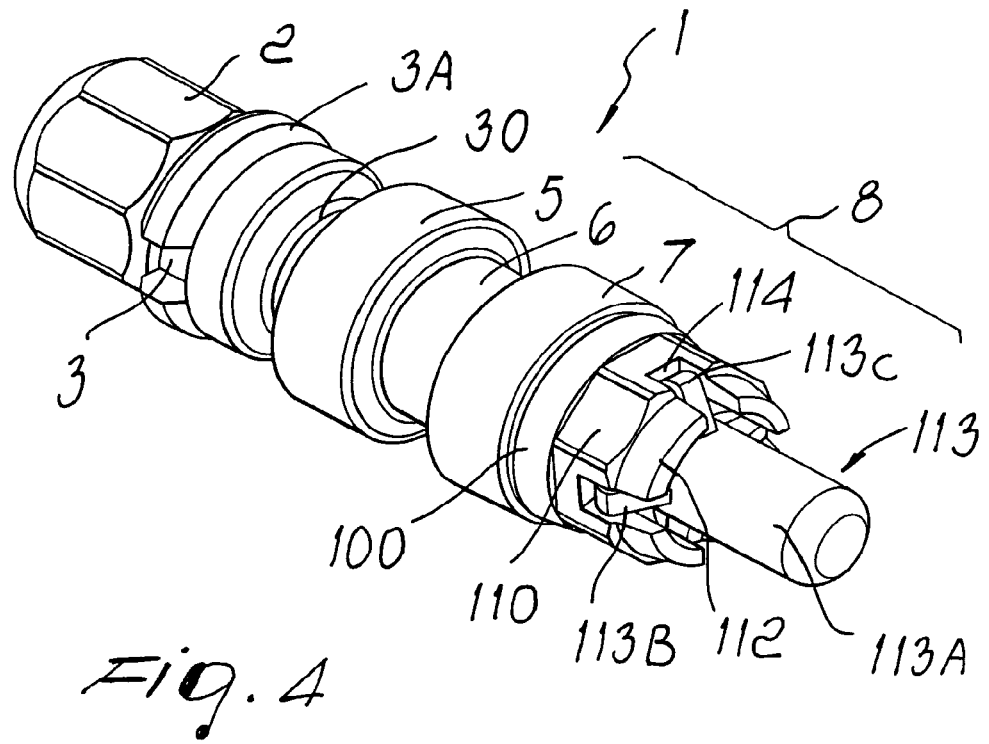
FIG. 4 is a perspective view of a holding element for a dental implant according to a first embodiment of the present invention.
Figure 4A:
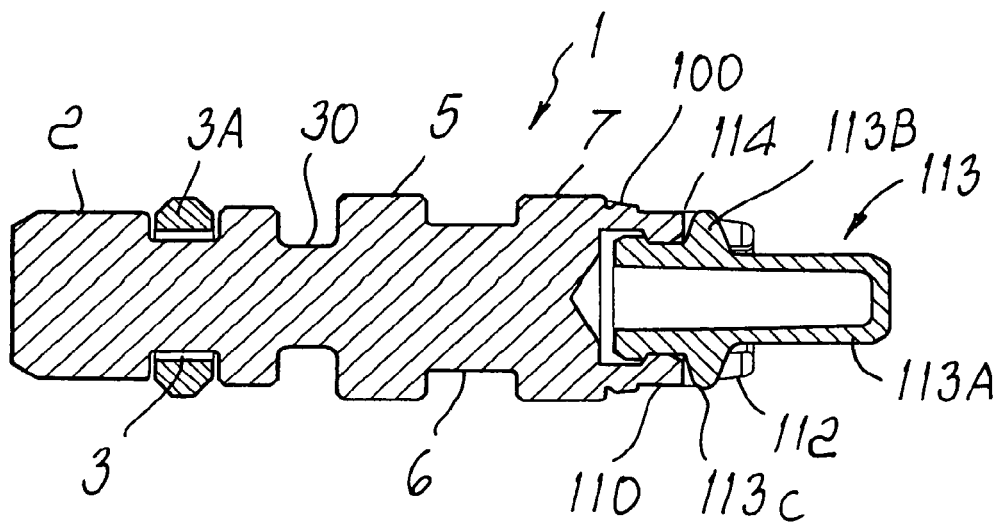
FIG. 4A is a cross-sectional view a holding element for a dental implant according to the first embodiment of the present invention.

With reference to FIGS. 4 and 4A there is described a holding element 1 for a dental implant according to a first embodiment of the present invention. It should be noted that elements thereof similar to those of FIGS. 1 through 3 are designated by the same reference numerals and that the description thereof will be omitted.

Figure 1:
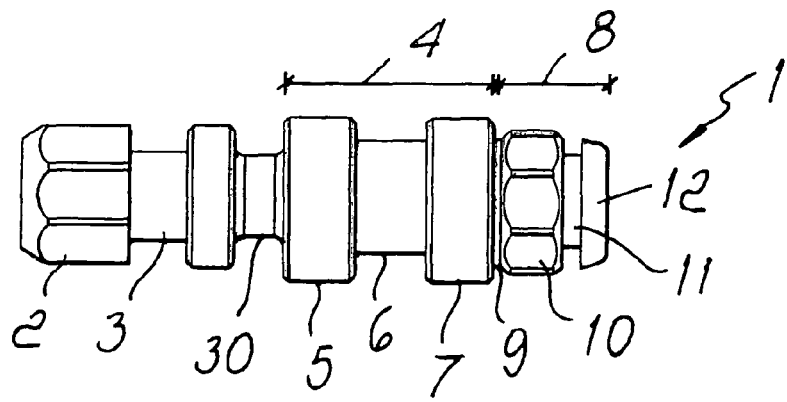
FIG. 1 is side view of a prior art holding element for a dental implant.
Figure 1A:
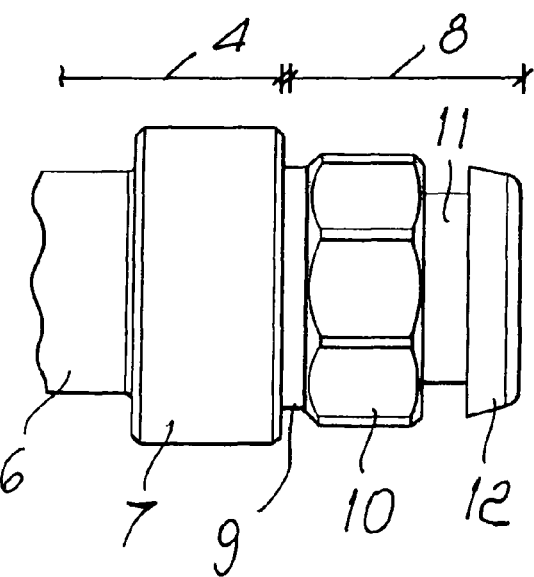
FIG. 1A is an enlarged view of a clamping section and of a retention section, in part, of the prior art holding element for a dental implant of FIG. 1.
Figure 2:
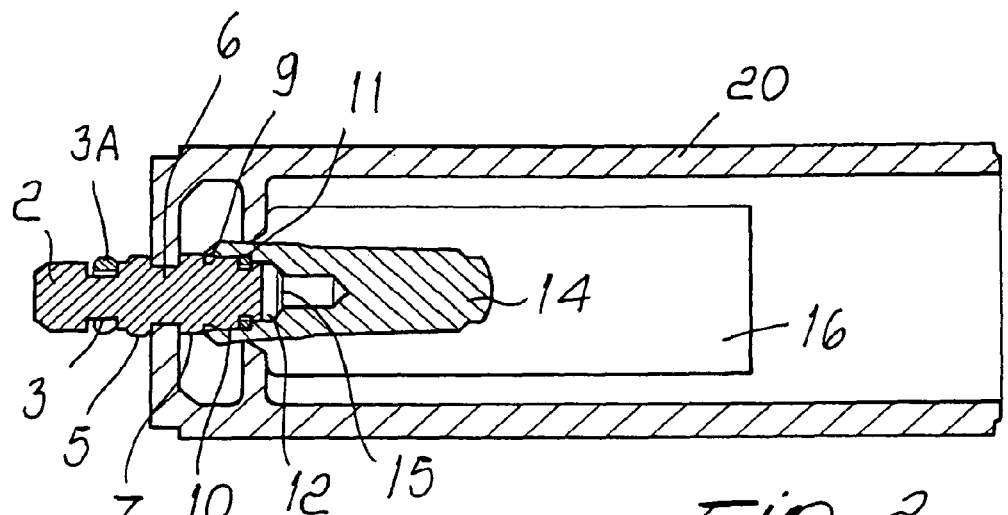
FIG. 2 is a sectional view of the holding element of FIG. 1 with a coupled dental implant and placed in an inner ampule for storage and transport of the dental implant.
Figure 2A:
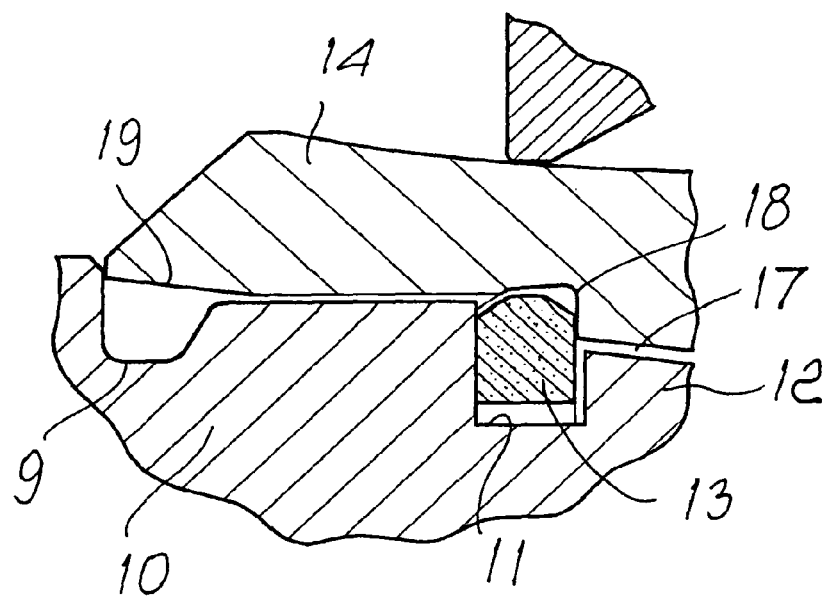
FIG. 2A is an enlarged sectional view of the clamping section of the holding element of FIGS. 1 and 2 when coupled to the dental implant.

As apparent from FIG. 4 the holding element 1 includes, in an similar manner to the prior art of FIGS. 1 through 3, the engagement section 2 for the positive engagement with a manipulating tool, the radial groove 3 for accommodating the O-ring 3A, preferably made of PEEK, the breaking point member 30, the retention section with the two adjoining annular shoulders 5 and 7 and the intermediate cylindrical section 6 of a reduced diameter, and a novel clamping section 8 to be described hereinbelow. The engagement section 2 of the present invention is preferably of polygonal and more preferably of octagonal shape.

The novel clamping section 8 according to the first embodiment of the present invention includes a first member 100 adapted for cooperation with the terminal section 19 of the dental implant 14 and connecting to the adjoining annular shoulder 7, a force transmission element 110 connecting to the first member 100, and a second member 112 connecting to the force transmission element 110. Preferably, the first and/or second members 100, 112 are slightly tapered. The force transmission element 110 is preferably polygonally and more preferably octagonally shaped. Nevertheless, the force transmission element 110 can also have a substantially cylindrical or conical shape.

The force transmission element 110 and the second member 112 axially surround a novel clamping member 113 devised and arranged in accordance with the invention.

As shown in FIGS. 4 and 4A the clamping member 113 is formed with a substantially cylindrical body 113A and one or more arms 113B extending radially through respective openings 114 provided in the second member 112 and in the force transmission element 110. Nevertheless, the person skilled in the art will appreciate that the openings 114 may be formed only in the second member 112, such that the radial arm or arms 113B would extend adjacent to the force transmission element 110.

The clamping member 113 has a certain elasticity, such that the arms 113B can be compressed radially with the extremities or protrusions 113C thereof extending in the non-compressed position beyond the perimeter defined by the force transmission element 110. If the opening 114 is only formed in the second member 112 the extremities or protrusions of the arms 113B would accordingly only extend in the non-compressed position beyond the perimeter defined by the second member 112, however, to an extent sufficient to provide the clamping cooperation with an undercut 18 (not shown) of the dental implant 14.

Preferably the implant holder 1 of the first embodiment, except for the O-ring 3A and the clamping member 113, is manufactured of titan with the latter being made of PEEK, although an appropriate plastic material can also be used.

Further, preferably, the force transmission element 110, if shaped octagonally, allows a plurality of rotational positions, with four radial arms 113B extending through non-adjacent surfaces thereof.

In a similar manner to the prior art of FIGS. 1 through 3, the cavity 15 of the dental implant 14 is provided with the undercut 18 (not shown in connection with FIGS. 4 and 4A) to accommodate the radial arms 113B in the non-compressed position thereof.

The clamping member 113 can be molded into a cavity of the holding element 1, as shown in FIG. 4A, and the extension of the cylindrical body 113A into the cavity 15 of the dental implant 1 and its size are such that a good connection stability is provided. In a similar manner the second member 112 may also be sized to closely fit the cavity 15 of the dental implant to improve the stability of the connection.

Figure 5:
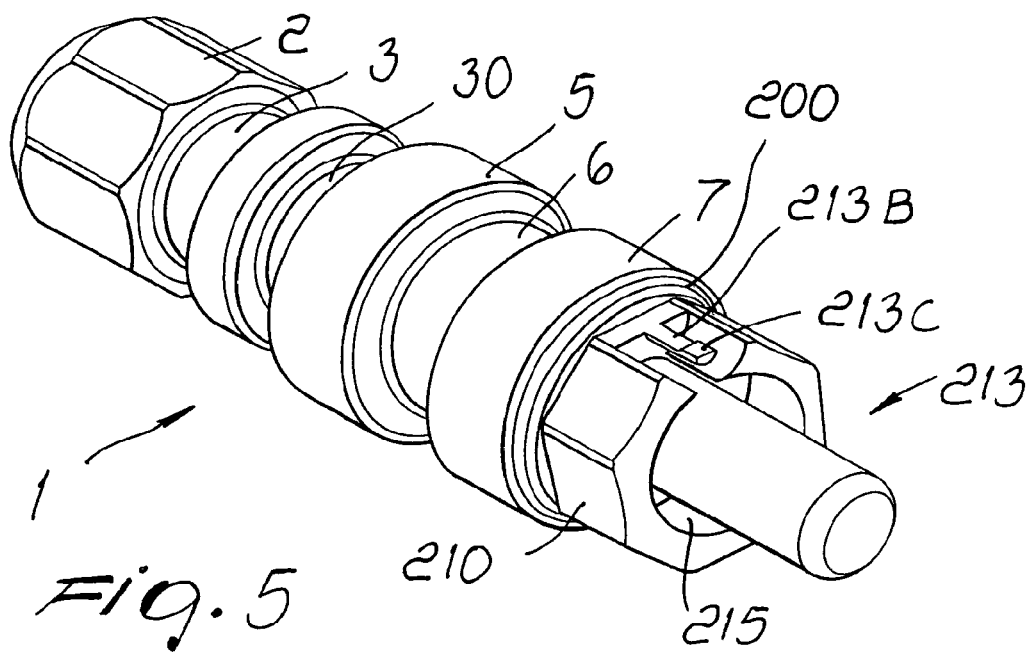
FIG. 5 is a perspective view of a holding element for a dental implant according to a second embodiment of the present invention.
Figure 5A:
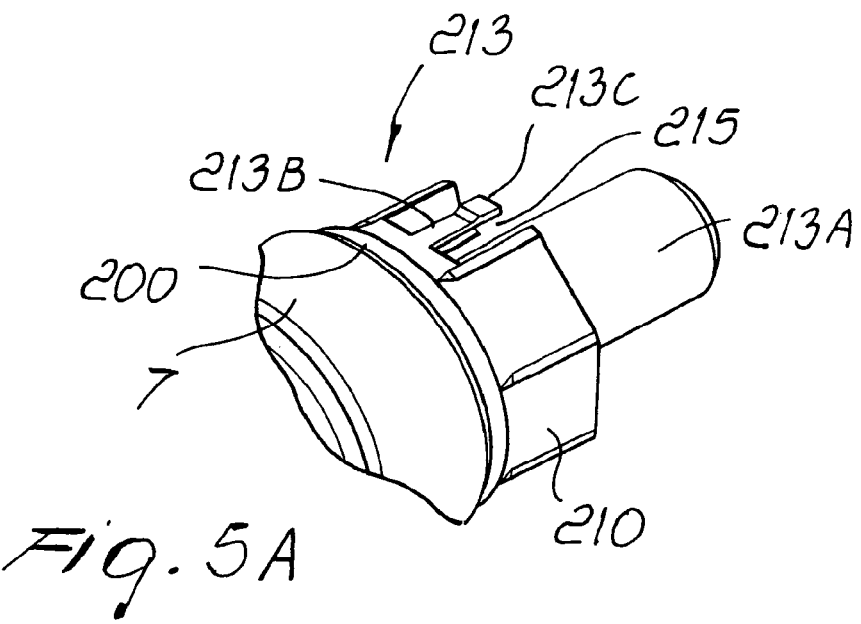
FIG. 5A is an enlarged view of the section of FIG. 5 including a clamping member.

With reference to FIGS. 5 and 5A there is described a holding element 1 for a dental implant according to a second embodiment of the present invention. It should be noted that elements thereof similar to those of FIGS. 1 through 4B are designated by the same reference numerals and that the description thereof will be omitted.

The novel clamping section 8 according to the second embodiment of the present invention includes a first member 200 adapted for cooperation with the terminal section 19 of the dental implant 14 and connecting to the adjoining annular shoulder 7 and a force transmission element 210 connecting to the first member 200. Preferably, the first member 200 is slightly tapered and the force transmission element 210 is preferably polygonal and more preferably octagonal. Nevertheless, the force transmission element 210 can also have a substantially cylindrical or conical shape.

A clamping member 213 according to the second embodiment of the invention, as particularly shown in FIG. 5A, includes an arm 213B which can be preferably milled from a lateral wall of the force transmission element 210. In a similar manner to the first embodiment the extremity or protrusion 213C of the arm 213B extends, in the non-compressed position thereof, beyond the perimeter defined by force transmission element 210, such as to lockingly engage an undercut 18 (not shown in connection with FIGS. 5 and 5A) provided in the cavity 15 of the dental implant 14.

Although one single arm 213B is shown in FIGS. 5 and 5A the person skilled in the art will appreciate that the number thereof can be variated, as need be.

The clamping section of the embodiment of FIGS. 5 and 5A further includes a substantially cylindrical body 213A extending from within the force transmission element 210 and sized to fit the cavity 15 of the dental implant 1 such that a good connection stability is provided. Preferably, a clearance shown at 215 is present between the inner surface of the force transmission element 210 and the cylindrical body 213A.

The holding element of the second embodiment, except for the not shown O-ring, is preferably made of titan.

Figure 6:
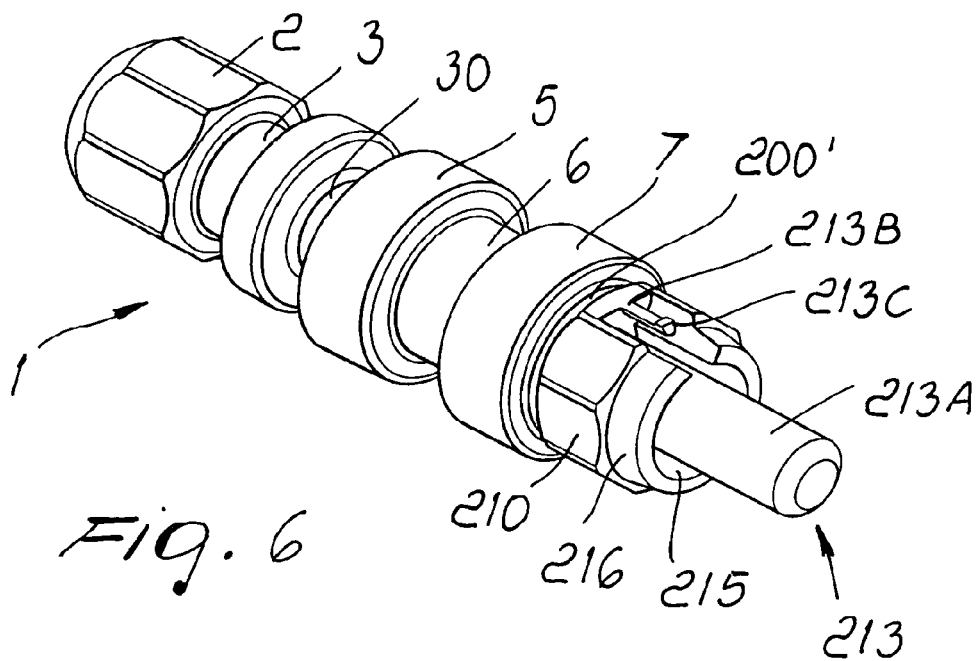
FIG. 6 is a perspective view of a holding element for a dental implant according to a third embodiment of the present invention.

With reference to FIG. 6 there is described a holding element 1 for a dental implant according to a third embodiment of the present invention. It should be noted that elements thereof similar to those of FIGS. 5 and 5A are designated by the same reference numerals and that the description thereof will be omitted. As shown in FIG. 6 the first member is devised as a circular groove 200' and there is provided a second member 216 protruding from the force transmission element 210 such as to further improve the stability of the connection between the holding element 1 and the dental implant 14.

Figure 7:
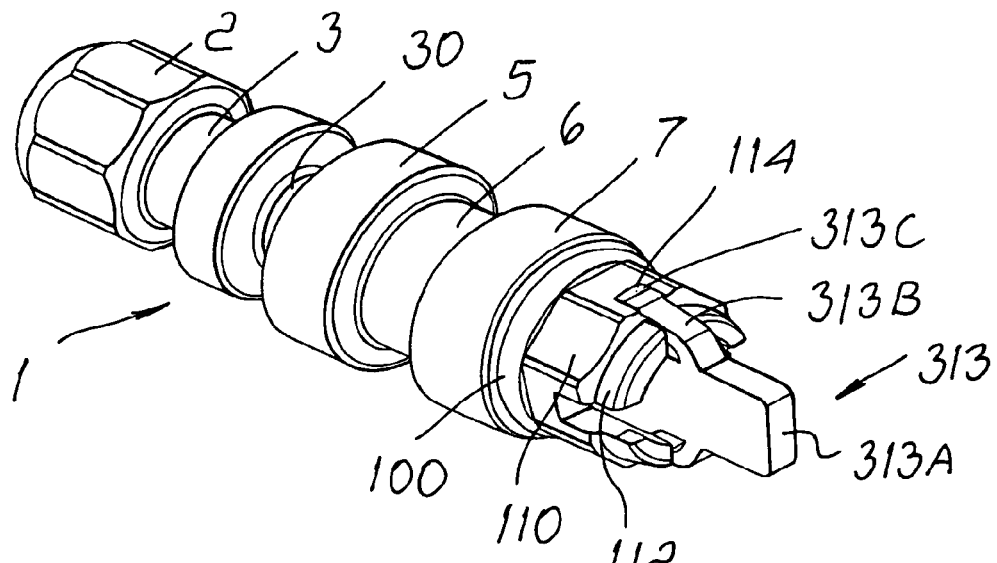
FIG. 7 is a perspective view of a holding element for a dental implant according to a fourth embodiment of the present invention.

With reference to FIG. 7 there is described a holding element 1 for a dental implant according to a fourth embodiment of the present invention. It should be noted that elements thereof similar to those of FIGS. 4 and 4A are designated by the same reference numerals and that the description thereof will be omitted. As shown in FIG. 7 the clamping member 313 includes a body 313A shaped substantially as a parallelepiped with preferably two arms 313B extending from a middle section of the parallelepiped body 313A. The arms 313B are provided with respective protrusions 313C. The clamping member 313 of the latter embodiment may be manufactured of PEEK or titan.

Figure 7A:
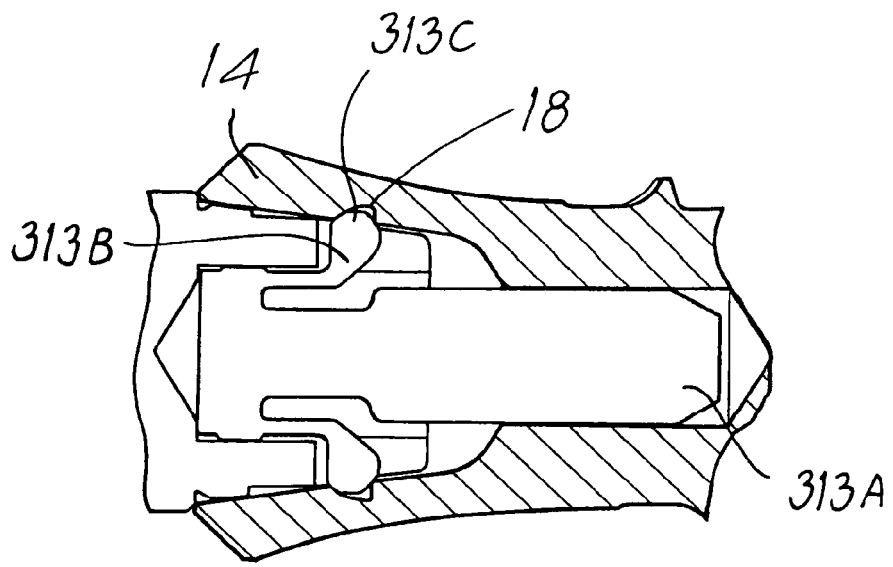
FIG. 7A is sectional view showing a variation of the fourth embodiment of FIG. 7 with the holding element shown engaged in the undercut of the dental implant.

In the variation of FIG. 7A the arms 313B extend from a lower section of the parallelepiped body 313A. Furthermore, in FIG. 7A the holding element 1 is shown engaged in the undercut 18 of the dental implant 14.

Figure 8:
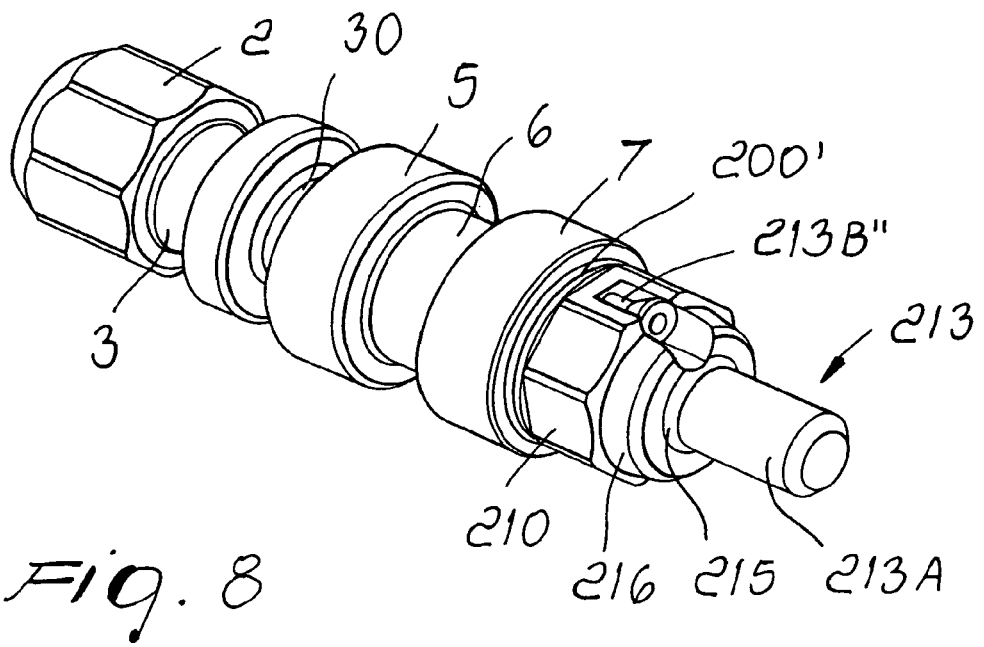
FIG. 8 is a perspective view of a holding element for a dental implant according to a fifth embodiment of the present invention.
Figure 8A:
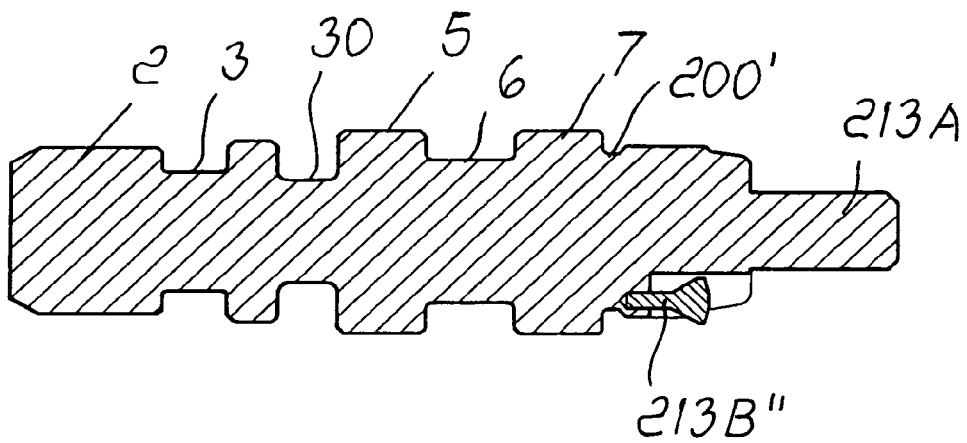
FIG. 8A is sectional view of FIG. 8.

With reference to FIGS. 8 and 8B there is described a holding element 1 for a dental implant according to a fifth embodiment of the present invention. It should be noted that elements thereof similar to those of FIG. 6 are designated by the same reference numerals and that the description thereof will be omitted. As shown in FIG. 8 the arm 213B" of the clamping element 213 is in the shape of a pinhead inserted into a recess provided in the force transmission element 210 and in the second member 216, with the pinhead shaped arm 213B" having a suitable elasticity. The clearance 215 between the inner surface of the force transmission element 210 and the cylindrical body 213A may be omitted in this embodiment, as shown in FIGS. 8 and 8A.

Figure 9:
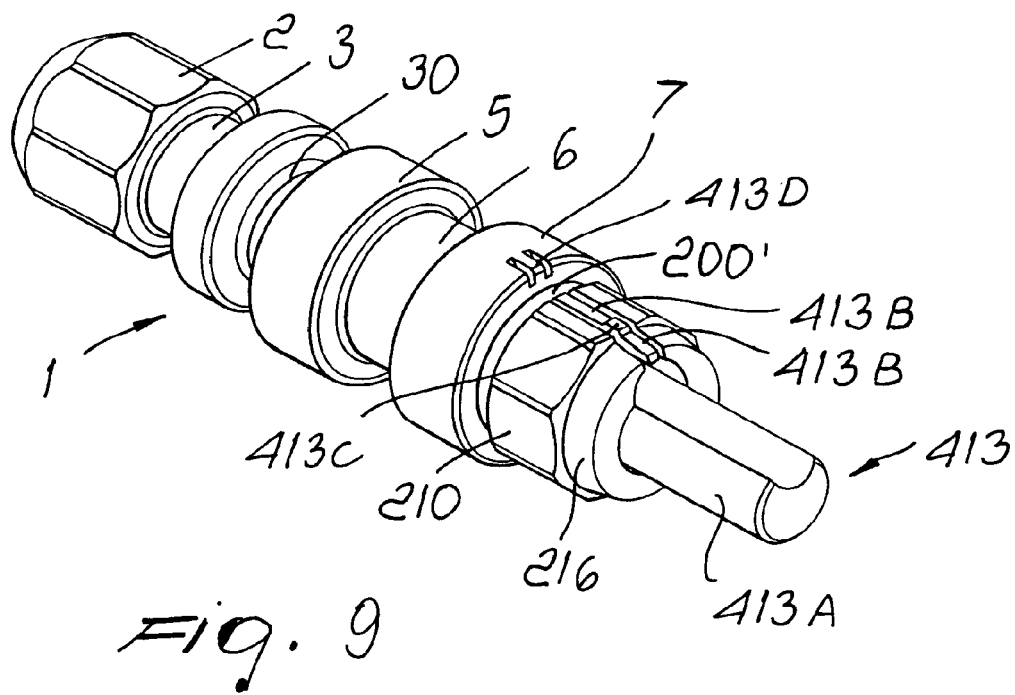
FIG. 9 is a perspective view of a holding element for a dental implant according to a sixth embodiment of the present invention.

With reference to FIG. 9 there is described a holding element 1 for a dental implant according to a sixth embodiment of the present invention. It should be noted that elements thereof similar to those of FIG. 6 are designated by the same reference numerals and that the description thereof will be omitted. In the sixth embodiment of the invention the clamping element 413 is provided by means of a flexible arm 413B formed as a clip extending parallel to the axis of the holding element 1. A protrusion 413C of the arm 413B extends yet again in the non-compressed position beyond the perimeter defined by the force transmission element 210. The clip can be milled or otherwise manufactured from a lateral wall of the force transmission element 210.

Further, advantageously, an additional flexible arm 413D in the shape of a clip may be provided on the annular shoulder 7 so as to further enhance the clamping force available for connecting the dental holder to the dental implant.

In the latter embodiment the clearance 215 between the inner surface of the force transmission element 210 and the cylindrical body 413A may also be omitted.

It is noted in respect to all of the above embodiments that the holding element of the present invention is intended to be stored in a package with or without a storage fluid. Further, the package may be possibly embodied as an ampule of the type described in the prior art publications WO-A1-2005/037126 or U.S. Pat. No. 6,261,097.

Clearly, several modifications will be apparent to and can be readily made by the skilled in the art without departing from the scope of the present invention. Therefore, the scope of the claims shall not be limited by the illustrations or the preferred embodiments given in the description in the form of examples, but rather the claims shall encompass all of the features of patentable novelty that reside in the present invention, including all the features that would be treated as equivalents by the skilled in the art.

The disclosures in EPA 05107165.2 from which this application claims priority are incorporated herein by reference.

What is claimed is:

1. A holding device for a dental implant, comprising:
    an engagement section adapted for engagement with a manipulating tool;
    a retention section joined to the engagement section and adapted for engagement with a package; and
    a clamping section joined to the retention section and adapted for connecting the holding device to the dental implant, the clamping section comprising a force transmission element,
    wherein the clamping section further comprises a clamping element provided with an elastic means extending in a non-compressed position thereof at and beyond an outer radial perimeter defined by the force transmission element, said elastic means comprising an elongated body extending in a longitudinal direction and at least one arm extending radially from the elongated body, the elongated body at least partially retained in a cavity of the holding device.

2. The holding device according to claim 1, wherein the elastic means extends in a non-compressed position thereof through a respective opening in the outer perimeter of the force transmission element.

3. The holding device according to claim 1, wherein the elongated body comprises a substantially cylindrical elongated body.

4. The holding device according to claim 3, wherein the elastic means comprises four radial arms and is preferably made of PEEK.

5. The holding device of claim 1, wherein the elongated body comprises a substantially parallelepiped elongated body.

6. The holding device according to claim 5, wherein the elastic means comprises two radial arms extending in a radial direction from a middle section of the body.

7. The holding device according to claim 5, wherein the elastic means comprises two radial arms extending in a radial direction from a section of the body which is situated at a bottom of the cavity of the holding device.

8. The holding device of claim 1, wherein the retention section is adapted for engagement with an ampule.

9. A holding device for a dental implant, comprising:
    an engagement section adapted for engagement with a manipulating tool;
    a retention section joined to the engagement section and adapted for engagement with a package; and a clamping section joined to the retention section and adapted for connecting the holding device to the dental implant, the clamping section comprising a force transmission element having an external profile adapted for rotationally securing the dental implant, wherein the clamping section further comprises a clamping element provided with an elastic means extending in a non-compressed position thereof at and beyond an outer radial perimeter defined by the force transmission element, said elastic means comprising at least one arm formed from a lateral wall of the force transmission element, said lateral wall defining at least a part of the external profile.

10. The holding device of claim 9, wherein the at least one arm extending parallel to a central axis of the holding device around which the outer profile of the holding device is substantially symmetrical.

11. The holding device of claim 9, wherein the at least one arm is milled from the lateral wall of the force transmission element.

12. A holding device for a dental implant, comprising:
an engagement section adapted for engagement with a manipulating tool;
a retention section joined to the engagement section and adapted for engagement with a package; and
a clamping section joined to the retention section and adapted for connecting the holding device to the dental implant, the clamping section comprising a force transmission element,
wherein the clamping section further comprises a clamping element provided with an elastic means extending in a non-compressed position thereof at and beyond an outer radial perimeter defined by the force transmission element, said elastic means comprising at least one pinhead inserted into a longitudinal recess provided in the force transmission element, the recess being substantially parallel to a central axis of the holding device around which the outer profile of the holding device is substantially symmetrical.

* * * * *